United States Patent
Hodgkinson

(10) Patent No.: US 7,126,122 B2
(45) Date of Patent: Oct. 24, 2006

(54) METHOD FOR DETERMINING THE SAFETY OF GAS MIXTURES

(75) Inventor: Elizabeth Jane Hodgkinson, Loughborough (GB)

(73) Assignee: Lattice Intellectual Property Limited, London (GB)

( * ) Notice: Subject to any disclaimer, the term of this patent is extended or adjusted under 35 U.S.C. 154(b) by 23 days.

(21) Appl. No.: 10/182,783

(22) PCT Filed: Jan. 30, 2001

(86) PCT No.: PCT/GB01/00365

§ 371 (c)(1),
(2), (4) Date: Jul. 3, 2003

(87) PCT Pub. No.: WO01/57499

PCT Pub. Date: Aug. 9, 2001

(65) Prior Publication Data

US 2004/0036023 A1   Feb. 26, 2004

(30) Foreign Application Priority Data

Feb. 4, 2000   (GB) ................... 0002535.3

(51) Int. Cl.
*G01J 5/02* (2006.01)
(52) U.S. Cl. ................................. 250/339.13
(58) Field of Classification Search ................ 250/345, 250/339.13, 343, 338, 338.5
See application file for complete search history.

(56) References Cited

U.S. PATENT DOCUMENTS 3,978,877 A   9/1976   Cox
4,958,076 A * 9/1990   Bonne et al. ................ 250/343
6,165,347 A * 12/2000  Warburton ................ 205/782.5
6,545,278 B1* 4/2003   Mottier et al. ......... 250/339.13

FOREIGN PATENT DOCUMENTS

| DE | 198 23 918   | 12/1999 |
| EP | 0 930 496    | 7/1999  |
| JP | SHO59-212738 | 12/1984 |
| JP | SHO62-273436 | 11/1987 |
| JP | HEI11-118712 | 4/1999  |

OTHER PUBLICATIONS

H.F. Coward et al.: "Limits of flammability of gases and vapours" National Bureau of Mines, BULLETIN 503, pp. 5 and 8 1952.
H.F. Coward, et al., "Limits of Flammability of Gases and Vapors", XP-002168672.

* cited by examiner

*Primary Examiner*—Albert J. Gagliardi
*Assistant Examiner*—Marcus Taningco
(74) *Attorney, Agent, or Firm*—Oblon, Spivak, McClelland, Maier & Neustadt, P.C.

(57) ABSTRACT

A method for determining the safety of a gas mixture containing first and second flammable components together with non-flammable components, comprises using an optical detector to make at least two measurements influenced by the concentration in the gas mixture of the first and second flammable components. The percentage lower explosion limit of the gas mixture is calculated by a method based on the combination of the measurements. The method leads to acceptably accurate results, despite the presence of other flammable component(s) in the gas mixture.

19 Claims, 4 Drawing Sheets

FIG. 2.
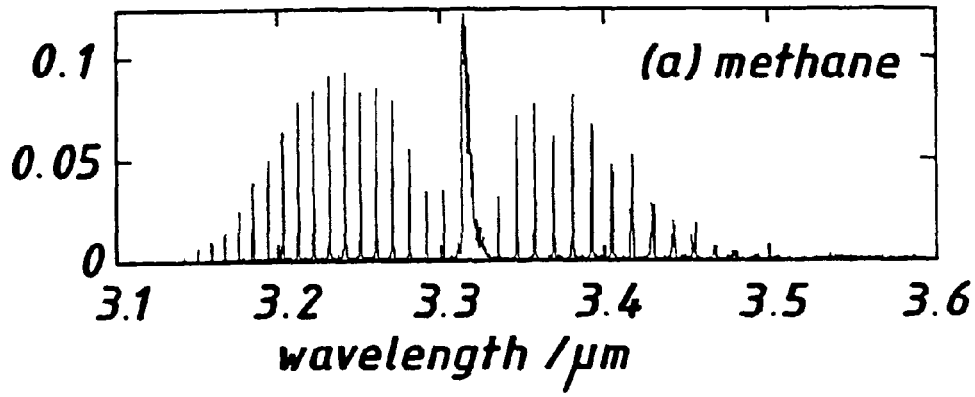
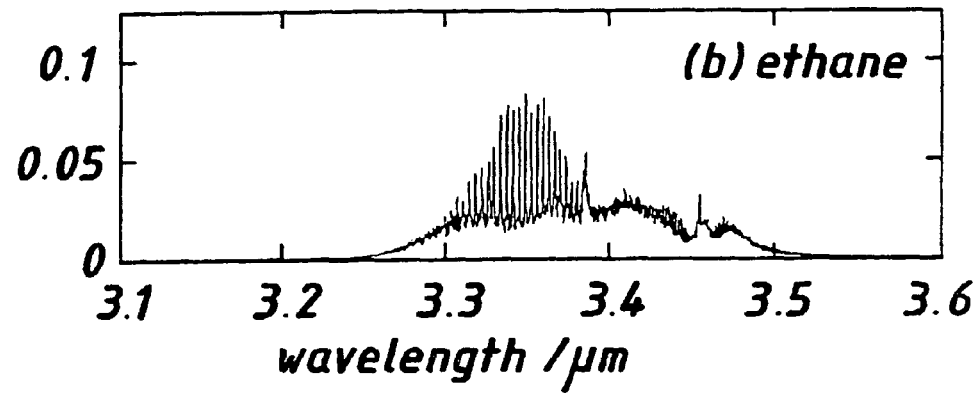
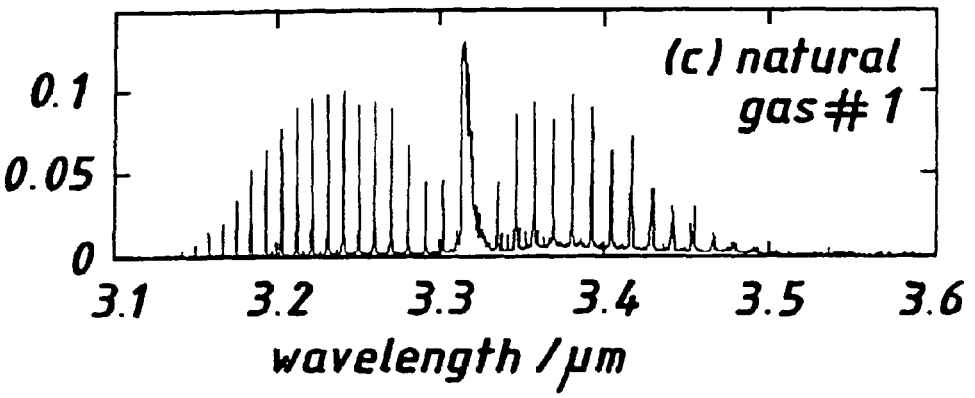

METHOD FOR DETERMINING THE SAFETY OF GAS MIXTURES

FIELD OF THE INVENTION

The present invention relates to a method for determining the safety of gas mixtures, in particular a gas mixture containing first and second flammable components together with at least one further flammable component and at least one non-flammable component.

BACKGROUND OF THE INVENTION

Flammable gas concentration measurements are made in a number of safety-critical situations. One such flammable gas is natural gas, which typically comprises mainly methane, plus higher hydrocarbons, inert gases and trace components. Natural gas detectors are needed for a number of applications including response to public reported gas escapes and for continuous monitoring of plant/equipment using permanently installed detectors. They are required to measure the gas concentration as a percentage of the lower explosion limit (LEL) of the gas mixture, this being an important safety parameter.

The required accuracy of gas detectors is given by international standards. For example, European Standard EN 50057:1999 specifies that the instrumental accuracy of such instruments shall be no more than either ±5% of the measuring range (usually 0–100% LEL) or ±10% of the reading, whichever is the greater. Some published company standards demand an even greater level of accuracy. None of the published standards for natural gas leak detectors specifically addresses the issue of measurement errors that arise from compositional variation in the gas, and base their requirements on the error when the detector is faced with a consistent composition. However, it is desirable to meet the required standards of accuracy even with gas compositions of inconsistent composition.

While methane-specific detectors (ie detectors with no cross-sensitivity to any other gas) have been used for determining the safety of natural gas mixtures, such devices do not have the necessary cross-sensitivity to other flammable components and can give large errors.

The most extensively used detectors are based on pellistor sensors or flame ionisation technology. Pellistor-based sensors work by oxidising the gas mixture on a heated catalyst bead. This provides a measure of combustibility that is inherently related to the % LEL of the natural gas leak. However, there are a number of associated problems with these sensors when detecting natural gas leaks:
i) The cross-sensitivity to different flammable gases is not exactly what is required to compensate for their differing LELs. Correction factors must be applied if the sensor is used to measure a gas species different from the gas used to calibrate it.
ii) So-called "foldback" of the sensor response, in that, if the gas is present in concentrations sufficient to displace large quantities of oxygen from the air, the gas cannot burn in the detector and its response actually decreases as the gas concentration increases. This can result in ambiguity of the reading in safety-critical situations.
iii) A high cost of ownership resulting from a high maintenance requirement.

A number of gas-specific detectors, mostly based on specific detection of methane, have been developed to overcome these difficulties for natural gas applications. Many use optical detection of the gas, and in particular measure the optical absorption of the methane or other gases at specific wavelengths in the infrared region of the electromagnetic spectrum. Examples include European patent specification 874233 A2 (Siemens AG). Methane is chosen because it is the principal component of natural gas. However, the other components of natural gas cause errors in the resulting % LEL reading. Because these components have a varying composition, it is not sufficient to calibrate out the systematic error; the remaining random error is still too large to meet the demands of the detector standards mentioned above.

SUMMARY OF THE INVENTION

According to the invention there is provided a method for determining the safety of a gas mixture containing first and second flammable components together with at least one further flammable component and at least one non-flammable component, comprising using an optical detector to make at least two measurements influenced by the concentration in the gas mixture of the first and second flammable components and calculating the percentage lower explosion limit of the gas mixture by a method based on the combination of the measurements.

Preferably, the percentage lower explosion limit of the gas mixture is calculated by a method based on the linear combination of the measurements. In broad terms, the percentage lower explosion limit (% LEL) is given by $$\% \ LEL = k_1 R_1 + k_2 R_2$$

where $R_1$ and $R_2$ are the two measurements influenced by the concentration in the gas mixture of the first and second flammable components and $k_1$ and $k_2$ are calibration constants for the optical detector.

The percentage lower explosion limit (% LEL) of the gas mixture is preferably calculated by use of the formula:

$$\% \ LEL = \frac{[A]}{LEL_A} + \frac{[B]}{LEL_B} \tag{1}$$

where [A] is the determined concentration of the first flammable component, [B] is the determined concentration of the second flammable component, $LEL_A$ is the lower explosion limit for the first flammable component, and $LEL_B$ is the lower explosion limit for the second flammable component.

The invention is particularly of advantage where the gas mixture includes further flammable components. In this event, the first and second flammable components are preferably the most predominant flammable components in the gas mixture. In particular, the gas mixture may be derived from natural gas which includes, for example, methane as the most predominant flammable gas, ethane or propane as the second most predominant gas and then other flammable gases, usually higher hydrocarbons, in relatively smaller amounts. The natural gas will typically be diluted with air in the gas mixture. The non-flammable components of the gas mixture will typically be nitrogen and oxygen derived from the air, carbon dioxide and various inert gases. We have surprisingly found that measuring the concentrations of the two principal flammable components of natural gas is sufficient to reduce composition variability errors to an acceptable level. Even though these and the other components of the gas mixture (including inert gases) could still vary, the method according to the invention results in an acceptably small error, well within international and published company standards. This makes the fundamental instrumental accuracy of an optical detector provide a similar level of compositional error as that of a pellistor-based detector, without the inherent disadvantages thereof. While the detection of concentrations of other less predominant flammable components may theoretically give more accurate % LEL readings, we have found that it is not a necessary requirement for gas detection applications.

Although the calculation of % LEL for two component mixtures from a measurement of the concentration of each of the two components is known from H F Coward and G W Jones in "Limits of flammability of gases and vapours"—National Bureau of Mines, Bulletin 503 (1952), it has not previously been proposed that an accurate measurement of % LEL for a multi-component gas mixture can be obtained by use of the method according to the invention.

In one possible embodiment of the invention, two measurements are made under species-specific conditions without cross-sensitivity, that is under conditions such that each measurement is indicative of the concentration of one of the flammable components but substantially not influenced by the concentration of the other of the flammable components. This embodiment may be realised by the use of an infrared spectrometer at high resolution or by the use of a tunable laser, as described in German patent application DE 19823918 (Siemens AG).

In an alternative embodiment of the invention, two measurements are made under cross-sensitive conditions, that is under conditions such that each measurement is influenced by the concentration of both the first and second flammable components. The degree of cross-sensitivity should be sufficient that both the first and second flammable components can be detected above the inherent noise of the optical detector. In this embodiment, it is preferred that one of the measurements is made under conditions such as to be influenced more by the concentration of the first flammable component than by the concentration of the second flammable component, while the other of the measurements is made under conditions such as to be influenced more by the concentration of the second flammable component than by the concentration of the first flammable component. This embodiment may be realised by the use of an infrared spectrometer with two low resolution filters, by the use of two LED/filter/detector combinations or by the use of a tunable laser.

It is also possible for one measurement to be made under non-cross-sensitive conditions while a second measurement is made under cross-sensitive conditions.

Whatever embodiment is adopted, the required resolution may be determined from knowing the nature of the predominant flammable components in the gas mixture and their IR spectra.

Preferably, the concentrations of the first and second flammable components in the gas mixture are measured by measuring the optical absorption in the infrared region in at least two distinct wavelengths. In this case, the optical detector may be an infrared spectrometer, which acts to detect at least one of the flammable components by measuring absorption at a characteristic infrared wavelength.

Where, for example, the first flammable component is methane, the concentration of methane in the gas mixture is preferably measured by measuring the optical absorption in the infrared region at a wavelength of between 1.62 and 1.72 µm or between 3.15 and 3.5 µm or between 7.25 and 8.2 µm.

Similarly, for example, where the second flammable component is ethane, the concentration of ethane in the gas mixture is preferably measured by measuring the optical absorption in the infrared region at a wavelength between 1.65 and 1.81 µm or between 3.23 and 3.55 µm or between 6.4 and 7.35 µm.

Where the gas mixture contains methane and ethane as the predominant flammable components, lines are chosen that do not overlap for gas specificity, i.e. a methane line is chosen for which ethane absorption is negligible and vice versa.

The invention also provides an apparatus for determining the safety of a gas mixture containing first and second flammable components together with at least one further flammable component and at least one non-flammable component, the apparatus comprising an optical detector to make at least two measurements influenced by the concentration in the gas mixture of the first and second flammable components and calculating means pre-programmed with data indicative of the lower explosion limits for the first and second flammable components and being programmed to calculate the percentage lower explosion limit of the gas mixture by a method based on the linear combination of said measurements.

The calculating means is preferably programmed to calculate the percentage lower explosion limit (% LEL) of the gas mixture by use of the formula:

$$\% \ LEL = \frac{[A]}{LEL_A} + \frac{[B]}{LEL_B} \quad (1)$$

where [A] is the measured concentration of the first flammable component, [B] is the measured concentration of the second flammable component, $LEL_A$ is the lower explosion limit for the first flammable component, and $LEL_B$ is the lower explosion limit for the second flammable component.

Other optical detectors which can be used in the present invention, as an alternative to (i) an infrared spectrometer, include (ii) devices to detect at least one of the flammable components using a broadband light source with an optional optical filter, the filter and light source combination allowing characteristic wavelengths to pass through the gas; (iii) devices to detect at least one of the flammable components using a broadband light source and a scanning filter; (iv) devices to detect at least one of the flammable components using a laser operating at a characteristic absorption wavelength; (v) devices to detect at least one of the flammable components using a scanning laser operating over a wavelength range containing at least one characteristic absorption line; (vi) devices to detect at least one of the flammable components using correlation spectroscopy; (vii) devices to detect at least one of the flammable components using photo-acoustic or photo-thermal spectroscopy; (viii) devices to detect at least one of the flammable components component using Raman spectroscopy; and (ix) devices to detect at least one of the flammable components component using an LED and detector, with an optional filter.

A particularly preferred alternative is to use a device capable of measuring an optical absorption over a range covering at least one absorption line of the first and second flammable components, such as a scanning laser.

The invention will now be further described, purely by way of example, with reference to the accompanying drawings, in which:

FIG. 2 shows mid infrared gas spectra determined with a Bio-Rad FTS-60A spectrometer at high resolution (0.25 cm$^{-1}$) using a 10 cm path length gas cell;

Figure 1:
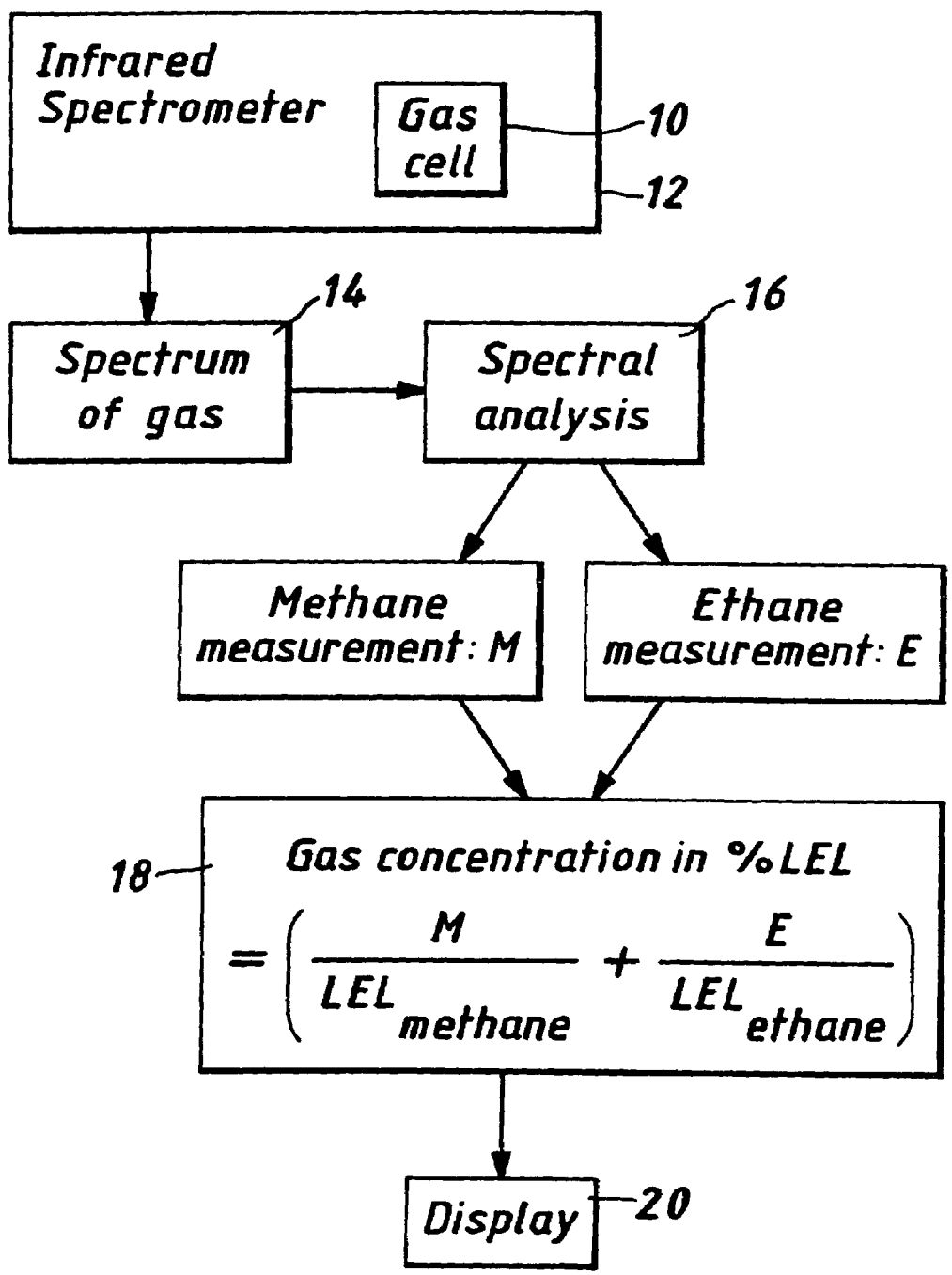
FIG. 1 is a block diagram showing natural gas concentration measurement on the % LEL scale using an infrared spectrometer.

One method of putting the present invention into effect is illustrated in FIG. 1. The gas mixture under investigation is placed in a gas cell 10, which is part of a FTIR (Fourier Transform InfraRed) spectrometer 12. The spectrometer produces a spectrum 14 of the gas mixture which is passed to a spectrum analysis device 16, where the absorption at predetermined wavelengths is examined to generate methane and ethane concentration measurements M and E respectively. A calculating device 18 then calculates the % LEL by use of the formula $$\% \, LEL = \frac{M}{LEL_{methane}} + \frac{E}{LEL_{ethane}} \quad (2)$$

and then displays this result to the user at a display device 20.

EXAMPLES

Infra-red spectra of gases of three different compositions, plus a methane control, were measured using the spectrometer for different concentrations of the gases in the 0–100% LEL range. The spectra were analysed to give a methane-specific concentration measurement and an ethane specific concentration measurement for each gas sample. The apparent concentration in % LEL was then deduced from these measurements using two methods; (i) based on the methane measurement only (equation (3)):

$$\% \, LEL = \frac{[methane]}{LEL_{methane}} \quad (3)$$

and (ii) based on the methane plus ethane measurement (equation (4)):

$$\% \, LEL = \frac{[methane]}{LEL_{methane}} + \frac{[ethane]}{LEL_{ethane}} \quad (4)$$

The results of these two methods were compared to show a lower spread of results for method (ii) than for method (i).

Experimental Details

The gas mixtures had the compositions given in Table 1.

TABLE 1

Compositions in mol % of three artificial gas mixtures typical of natural gas.

| Gas component | Sample #1 | Sample #2 | Sample #3 |
| --- | --- | --- | --- |
| nitrogen | 1.72 | 2.21 | 0.731 |
| carbon dioxide | 0.32 | 0.8 | 2.11 |
| methane | 93.55 | 92.86 | 86.48 |
| ethane | 3.27 | 3.02 | 7.47 |
| propane | 0.763 | 0.635 | 2.5 |
| i-butane | 0.122 | 0.131 | 0.182 |
| n-butane | 0.153 | 0.156 | 0.392 |
| n-pentane | 0.103 | 0.18 | 0.13 |
| C6+ alkanes | 0.0 | 0.0002 | 0.0003 |
| LEL/% vol. | 4.89% vol | 4.94% vol | 4.63% vol |

In this table, LELs have been calculated according to the method given by H F Coward and G W Jones in "Limits of flammability of gases and vapours"—National Bureau of Mines, Bulletin 503 (1952), referred to above. This calculation was performed using data on the LELs of the individual gas components taken from European Standard EN 50054:1991.

The natural gases at 100% were blended with hydrocarbon free air in varying proportions. The concentration was determined using a Luft infrared methane analyser (ADC 0/8Z/35/H) which was separately adjusted for the cross-sensitivity to the other components of each gas mixture to give an accurate reading for each. Thus, the actual % LEL of each gas mixture was determined from the concentration of the sample gas in the gas mixture.

Gas spectra were measured using a 10 cm path length gas cell. Spectra were measured in two regions of the infrared; the near infrared (centred around 1.65 µm) and in the mid infrared (centred around 3.3 µm). The noise and linearity performance of the spectrometer were better, at the concentrations used, in the mid infrared region, so these spectra were used to analyse gases over a range of concentrations. However, the analysis could equally apply to the 1.65 µm region spectra, given better spectrometer performance, since these spectra are similar to the 3.3 µm spectra (being an overtone of that fundamental vibration). To confirm this, the analysis was repeated for the near infrared spectra of different gas mixtures at a single (high) concentration. The analysis would also apply to the region of known spectral absorption from 6.4 µm to 8.2 µm.

The spectrometer (Bio-Rad FTS-60A) was set up according to the manufacturer's instructions, for high resolution mid infrared spectroscopy. For mid infrared measurements a high temperature ceramic light source was used, with a wide band KBr beam splitter and liquid nitrogen cooled MCT detector, all of these options supplied with the spectrometer. KBr windows were also used in the gas cell. For near infrared measurements, a quartz halogen light source, quartz beamsplitter, InGaAs detector and silica windows were used. The highest available resolution (0.25 cm$^{-1}$) was chosen.

Spectra from the sample gases were corrected for cell absorptions and reflections by subtraction of a reference spectrum, taken with the cell filled with hydrocarbon free air. For each spectrum, a baseline zero was established by interpolation of a straight line between the average absorption in the following two regions of the mid infrared: (i) 3.05–3.1 µm, and (ii) 3.65–3.7 µm, and in the following two regions of the near infrared: (i) 1.55 µm–1.59 µm, (ii) 1.85

µm–1.90 µm. These regions were chosen for their insignificant levels of absorption for natural gas. Methane and ethane measurements were each established by taking the height of the absorption at one characteristic wavelength, corresponding to an absorption line of that gas. In the mid infrared for methane a wavelength of 3.167 µm was chosen, and 3.348 µm for ethane. The absorption of methane at 3.167 µm was relatively low, which minimised the non-linearities at high concentrations due to saturation effects arising from Beer's Law. In contrast, the absorption of ethane at 3.348 µm was relatively high, chosen to maximise the signal to noise ratio for this species, which occurs in relatively low quantities in natural gas. Cross-sensitivity checks established that the level of ethane absorption at the methane wavelength was negligible, and vice versa. Using this technique, the instrumental zero repeatability was established to be $<10^{-4}$ cm$^{-1}$. The level of repeatability for a repositioned cell containing 2.5% methane (50% LEL) was similarly found to be below 1% of the measurement. In the near infrared, the same approach was adopted, with 1.643 µm chosen as the methane measurement wavelength and 1.683 µm chosen for ethane.

Experimental Results

A typical mid infrared spectrum of natural gas, measured using the FTIR spectrometer, is shown in FIG. 2. Also shown are measured spectra of pure methane in air and of pure ethane in air. The calculated baseline zero has been subtracted in each case.

These spectra were analysed in the following way. The height of the gas absorption lines at the wavelengths indicated above (characteristic of methane and ethane) were found from the measured spectra. These measurements were proportional to the gas concentrations, except that at high concentrations of methane, a small level of instrumental non-linearity caused a slight non-linearity in the measurements. These measurements were analysed according to the following equations;

(i) Response $R=aM$ (i) Response $R'=aM+bE$ (5)

where M and E are the measured spectral absorptions at wavelengths corresponding to the methane and ethane absorption lines, respectively, and a and b are calibration factors that relate the absorption levels at those wavelengths to gas concentrations. The value of a was determined by reference to the results for the methane control. The values of a and b were calibrated by reference to the known amounts of methane and ethane in each mixture. For mid infrared data, the values were chosen to be a=39.2 and b=1.41. For near infrared data, the values were a=494 and b=1237.

Figure 3:
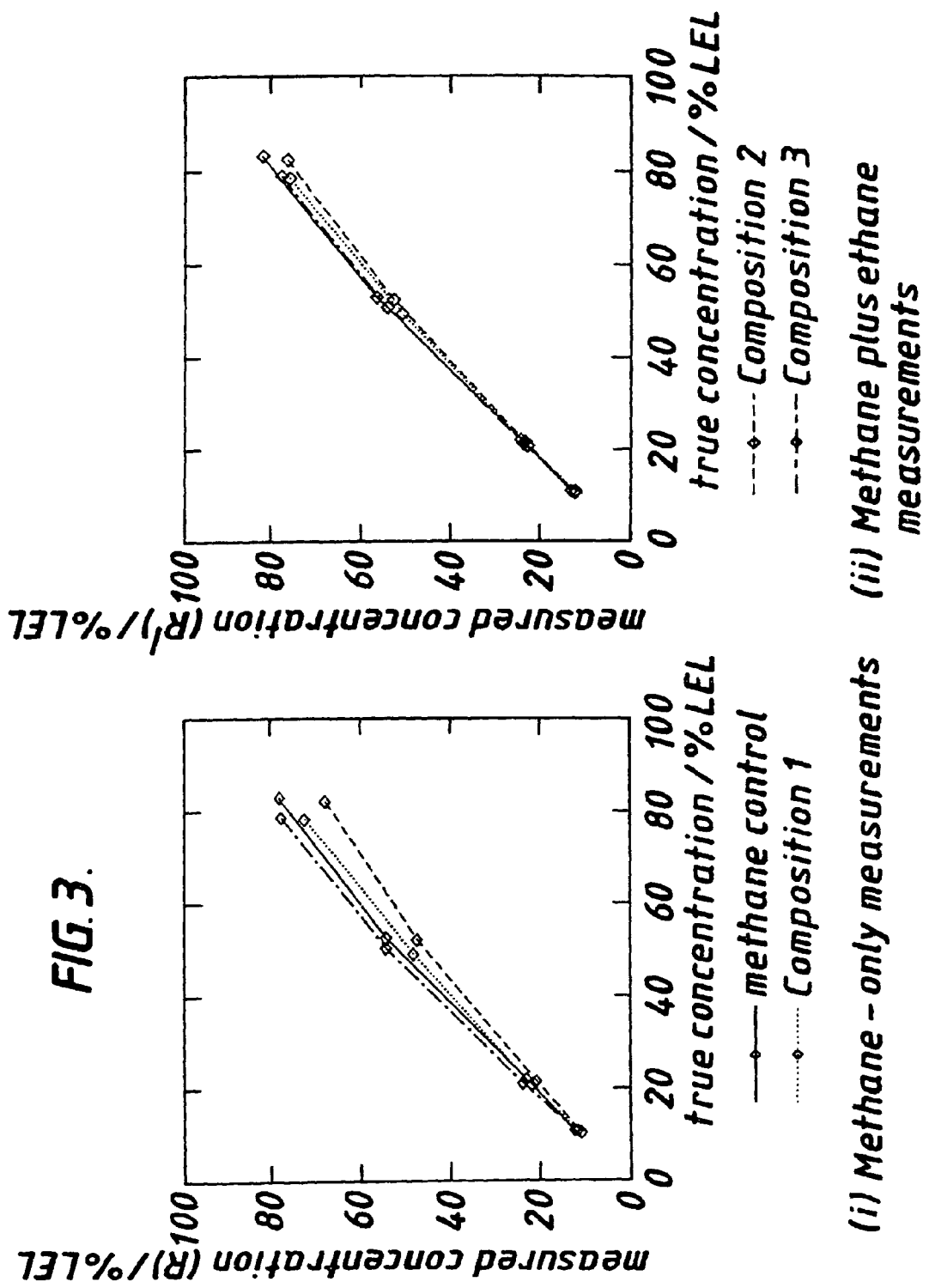
FIG. 3 shows experimental results from spectroscopic measurements of gas concentration.

The results in FIG. 3 show the measured % LEL (R and R" from equation (5)) for each gas mixture versus the reference % LEL, for the two cases (i) methane-only based measurements and (ii) methane plus ethane based measurements taken in the mid infrared. The spread of results for methane plus ethane measurements is clearly much lower than for methane-only measurements. A small amount of instrumental non-linearity can be seen to affect results for high methane concentrations, for all the natural gases and the methane control. It can clearly be seen that the spread of the results for different gas compositions is significantly reduced for method (ii).

Figure 4:
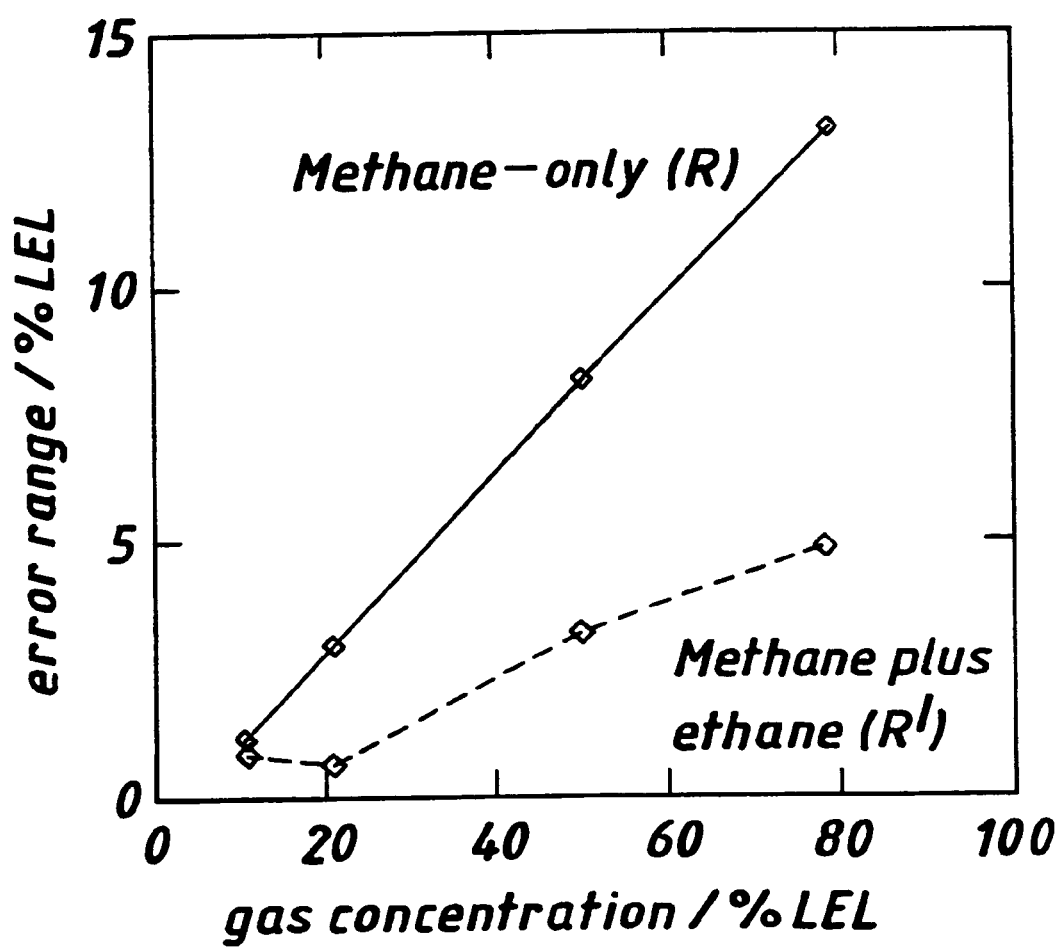
FIG. 4 shows the comparison of the range of experimental errors due to compositional variation at a number of gas concentrations.

A comparison can be made between the error in the measured % LEL for each gas sample with the error in the methane control, by subtracting the latter from the former. This takes account of the instrumental non-linearities that affected the results at high methane concentrations. Published gas standards specify that gas detectors must be able to perform under all specified conditions, rather than specifying a mean performance level. Therefore, the range of composition variation errors has been plotted in FIG. 4 rather than the mean error for each concentration. Methane plus ethane-based measurements have clearly reduced the range of errors compared to methane-only measurements in the mid infrared. Furthermore, in the near infrared the range of proportional errors was similarly reduced from 8% to 4%. Thus, the efficacy of the technique for measurements made in both the mid infrared and near spectual regions is confirmed.

The invention claimed is:

1. A method for determining the safety of a gas mixture containing first and second flammable components together with at least one further flammable component and at least one non-flammable component, comprising making at least two measurements of the concentrations of the first and/or second flammable components of the gas mixture with an optical detector and calculating the percentage lower explosion limit of the gas mixture by a method based on the combination of the measurements, wherein two measurements are made under conditions such that each measurement is influenced by the concentration of both the first and second flammable components.

2. A method according to claim 1, wherein the percentage lower explosion limit of the gas mixture is calculated by a method based on the linear combination of the measurements.

3. A method according to claim 2, wherein the percentage lower explosion limit (% LEL) of the gas mixture is calculated by use of the formula:

$$\% \ LEL = \frac{[A]}{LEL_A} + \frac{[B]}{LEL_B} \quad (1)$$

where [A] is the determined concentration of the first flammable component, [B] is the determined concentration of the second flammable component, $LEL_A$ is the lower explosion limit for the first flammable component, and $LEL_B$ is the lower explosion limit for the second flammable component.

4. A method according to claim 1, wherein the gas mixture is derived from natural gas.

5. A method according to claim 1, wherein two measurements are made under conditions such that each measurement is indicative of the concentration of one of the flammable components but substantially not influenced by the concentration of the other of the first and second flammable components.

6. A method according to claim 1, wherein one of the measurements is made under conditions such as to be influenced more by the concentration of the first flammable component than by the concentration of the second flammable component, while the other of the measurements is made under conditions such as to be influenced more by the concentration of the second flammable component than by the concentration of the first flammable component.

7. A method according to claim 1, wherein the concentrations of the first and second flammable components in the gas mixture are measured by measuring the optical absorption in the infrared region in at least two distinct wavelengths.

8. A method according to claim 1, wherein the first flammable component is methane.

9. A method according to claim 8, wherein the concentration of methane in the gas mixture is measured by measuring the optical absorption in the infrared region at a wavelength of between 1.62 and 1.72 µm or between 3.15 and 3.5 µm or between 7.25 and 8.2 µm.

10. A method according to claim 1, wherein the second flammable component is ethane.

11. A method according to claim 10, wherein the concentration of ethane in the gas mixture is measured by measuring the optical absorption in the infrared region at a wavelength between 1.65 and 1.81 µm or between 3.23 and 3.55 µm or between 6.4 and 7.5 µm.

12. The method according to claim 1, wherein said gas mixture comprises natural gas.

13. The method according to claim 1, wherein said first and second flammable components are the most predominant flammable components in said gas mixture.

14. An apparatus for determining the safety of a gas mixture containing first and second flammable components together with at least one further flammable component and at least one non-flammable component, the apparatus comprising an optical detector capable of making at least two measurements of the concentrations of the first and second flammable components of the gas mixture and calculating means capable of being pre-programmed with data indicative of the lower explosion limits for the first and second flammable components and capable of being programmed to calculate the percentage lower explosion limit of the gas mixture by a method based on the combination of said measurements, wherein two measurements are made under conditions such that each measurement is influenced by the concentration of both the first and second flammable components.

15. An apparatus according to claim 14, wherein the calculating means is programmed to calculate the percentage lower explosion limit of the gas mixture by a method based on the linear combination of said measurements.

16. An apparatus according to claim 15, wherein the calculating means is programmed to calculate the percentage lower explosion limit (% LEL) of the gas mixture by use of the formula:

$$\% \ LEL = \frac{[A]}{LEL_A} + \frac{[B]}{LEL_B} \tag{1}$$

where [A] is the measured concentration of the first flammable component, [B] is the measured concentration of the second flammable component, $LEL_A$ is the lower explosion limit for the first flammable component, and $LEL_B$ is the lower explosion limit for the second flammable component.

17. An apparatus according to claim 14, wherein said optical detector is an infrared spectrometer.

18. An apparatus according to claim 14, wherein said optical detector is a device capable of measuring an optical absorption over a range covering at least one absorption line of the first and second flammable components.

19. An apparatus according to claim 14, wherein said calculating means is pre-programmed with data indicative of the lower explosion limits for the first and second flammable components and is programmed to calculate the percentage lower explosion limit of the gas mixture by a method based on the combination of said measurements.

* * * * *